(12) United States Patent
Might et al.

(10) Patent No.: US 7,443,293 B2
(45) Date of Patent: Oct. 28, 2008

(54) CRYPTOGRAPHIC CONTAINER SECURITY SYSTEM

(75) Inventors: Matthew B. Might, Atlanta, GA (US); Mark A. Ferderer, Buford, GA (US); Gary F. Bowser, Auburn, IN (US)

(73) Assignee: ScanTech Holdings, LLC, Atlanta, GA (US)

( * ) Notice: Subject to any disclaimer, the term of this patent is extended or adjusted under 35 U.S.C. 154(b) by 222 days.

(21) Appl. No.: 11/259,738

(22) Filed: Oct. 24, 2005
(Under 37 CFR 1.47)

(65) Prior Publication Data
US 2007/0248212 A1    Oct. 25, 2007

Related U.S. Application Data

(60) Provisional application No. 60/621,376, filed on Oct. 22, 2004.

(51) Int. Cl.
*G08B 13/14* (2006.01)
(52) U.S. Cl. .............. 340/568.1; 430/572.1; 430/572.4; 430/539.31
(58) Field of Classification Search .............. 340/568.1, 340/571, 572.1, 572.4, 539.1, 539.26, 539.29, 340/539.31, 539.32, 600; 378/57, 62; 705/1
See application file for complete search history.

(56) References Cited

U.S. PATENT DOCUMENTS

| 3,828,193 | A  | * | 8/1974 | Nelson | .................... | 378/86 |
| 5,057,268 | A  |   | 10/1991 | Muller | | |
| 6,108,636 | A  |   | 8/2000 | Yap et al. | | |
| 6,370,222 | B1 |   | 4/2002 | Cornick, Jr. | | |
| 6,891,470 | B2 | * | 5/2005 | Bohinc, Jr. | .............. | 340/539.26 |
| 7,012,529 | B2 | * | 3/2006 | Sajkowsky | ............... | 340/572.1 |
| 7,176,800 | B2 | * | 2/2007 | Sajkowsky | ............... | 340/572.1 |

* cited by examiner

*Primary Examiner*—Van T. Trieu
(74) *Attorney, Agent, or Firm*—Coursey IP Law, PC; R. Stevan Coursey (57) ABSTRACT

A cryptographic container security system for enabling the secure transportation of a container from a sender site to a receiver site. The system includes, in the exemplary embodiment, apparatuses and methods for generating pre-transportation and post-transportation fingerprints of a container being transported, for encrypting and decrypting the pre-transportation fingerprint, and for comparing pre-transportation and post-transportation fingerprints, and for comparing the decrypted pre-transportation fingerprint and the pre-transportation fingerprint. The pre-transportation and post-transportation fingerprints are generated from fingerprint data, including, without limitation, the aggregate gamma flux and aggregate effective Z-number determined for the container by multi-energy scanning systems located, respectively, at sender and receiver sites.

31 Claims, 4 Drawing Sheets

CRYPTOGRAPHIC CONTAINER SECURITY SYSTEM

CROSS REFERENCE TO RELATED APPLICATION

This application claims the benefit of priority to U.S. provisional patent application Ser. No. 60/621,376 entitled "Cryptographic Container Security System for Container Transportation" and filed on Oct. 22, 2004, now pending.

FIELD OF THE INVENTION

The present invention relates, generally, to the field of cryptographic security systems and, more specifically, to cryptographic security systems for use with containers employed, generally, in the transportation industry.

BACKGROUND OF THE INVENTION

In today's global economy, goods consumed in a particular country may be produced or manufactured in another country on the other side of the world. After such goods are manufactured in a country, they are often loaded into containers with the containers then being transported by truck and/or rail from manufacturing plants to seaports, airports, or rail ports. There, the containers bearing the manufactured goods, or items, are on-loaded onto ships, airplanes, or railroad cars and are transported by the ships, airplanes, and railroad cars to seaports, airports, or rail ports of destination countries. Once off-loaded from the ships, airplanes, or railroad cars, the containers are transported, typically, by trucks and/or by other vehicles to distribution centers or warehouses in destination countries. During their journey between manufacturing and destination countries, the ships, airplanes, and rail cars transporting the containers may stop at a number of locations to on-load and/or off-load other containers or cargo and there is always the possibility that a particular container may be tampered with while the ships, airplanes, and rail cars are stopped at such locations. There is also the possibility, although more likely for containers that are transported by ships than by airplanes or rail cars, that a particular container may be tampered with while its ship is on the high seas.

Due to recent terrorist activities and because only a small percentage of such containers are, typically, inspected upon entering a country, many are deeply concerned that a terrorist may intercept one or more containers during their transportation and place high explosives, nuclear bombs, "dirty" bombs, harmful and/or deadly chemical and/or biological agents, or other weapons of mass destruction therein as part of a terrorist attack on a destination city or, for that matter, any location along a container's subsequent transportation route. Many are also concerned that a terrorist may simply load a container with one or more weapons of mass destruction and, using a false identity, place the container into the worldwide container transportation system as part of a terrorist attack.

Therefore, there exists in the industry, a need for a system that enables the secure transportation of a container from a sender site to a receiver site, and that addresses the above described, and other, problems, difficulties, and/or shortcomings of current systems.

SUMMARY OF THE INVENTION

Broadly described, the present invention comprises a system, including apparatuses and methods, for enabling the secure transportation of a container from a sender site to a receiver site. More particularly, the present invention comprises a system, including apparatuses and methods, for aiding in determining whether the a container or the contents of the container have been altered during its transportation and in determining whether a received container was digitally signed by the container's original sender as opposed to being digitally signed by an intermediate party.

The present invention is embodied, in the exemplary embodiment described herein, as a cryptographic container security system having a sender container encryption system located at a sender site and a receiver container decryption system located at a receiver site. The sender container encryption system includes a sender computer system and a sender fingerprinting system. The receiver container decryption system, similarly, includes a receiver computer system and a receiver fingerprinting system. The sender and receiver fingerprinting systems comprise multi-energy scanning systems that are operable to generate fingerprint data representative of the container and the contents present within the container, respectively, before and after transportation from the sender site to the receiver site. The fingerprint data includes, without limitation, the aggregate gamma flux and aggregate effective Z-number for the container.

The sender and receiver computer systems of the exemplary embodiment are operable to compute respective pre-transportation and post-transportation fingerprints for the container using, respectively, generated pre-transportation fingerprint data and generated post-transportation fingerprint data. The sender computer system is further operable to encrypt a computed pre-transportation fingerprint using a private key known only to the sender of the container, and to output the pre-transportation fingerprint and encrypted pre-transportation fingerprint to a media, device, or form suitable for direct or indirect attaching or securing to the container prior to transportation. The receiver computer system is further operable to read the pre-transportation fingerprint and the encrypted pre-transportation fingerprint from the media, device, or form attached or secured to the container prior to transportation, to decrypt the encrypted pre-transportation fingerprint, to compare the read pre-transportation fingerprint and a generated post-transportation fingerprint, and to compare the decrypted pre-transportation fingerprint and the read pre-transportation fingerprint. The receiver computer system is still further operable to determine, based on such comparisons, whether it is probable that the container or the contents of the container have not been altered during its transportation and whether the container was digitally signed by the container's original sender as opposed to being digitally signed by an intermediate party.

Advantageously, the present invention provides a system and methods for enabling the secure transportation of a container from a sender site to a receiver site. The present invention also provides a system and methods for, in a timely manner, determining whether a container has been tampered with during transportation.

Other advantages and benefits of the present invention will become apparent upon reading and understanding the present specification when taken in conjunction with the appended drawings.

DETAILED DESCRIPTION OF THE INVENTION

Figure 1:
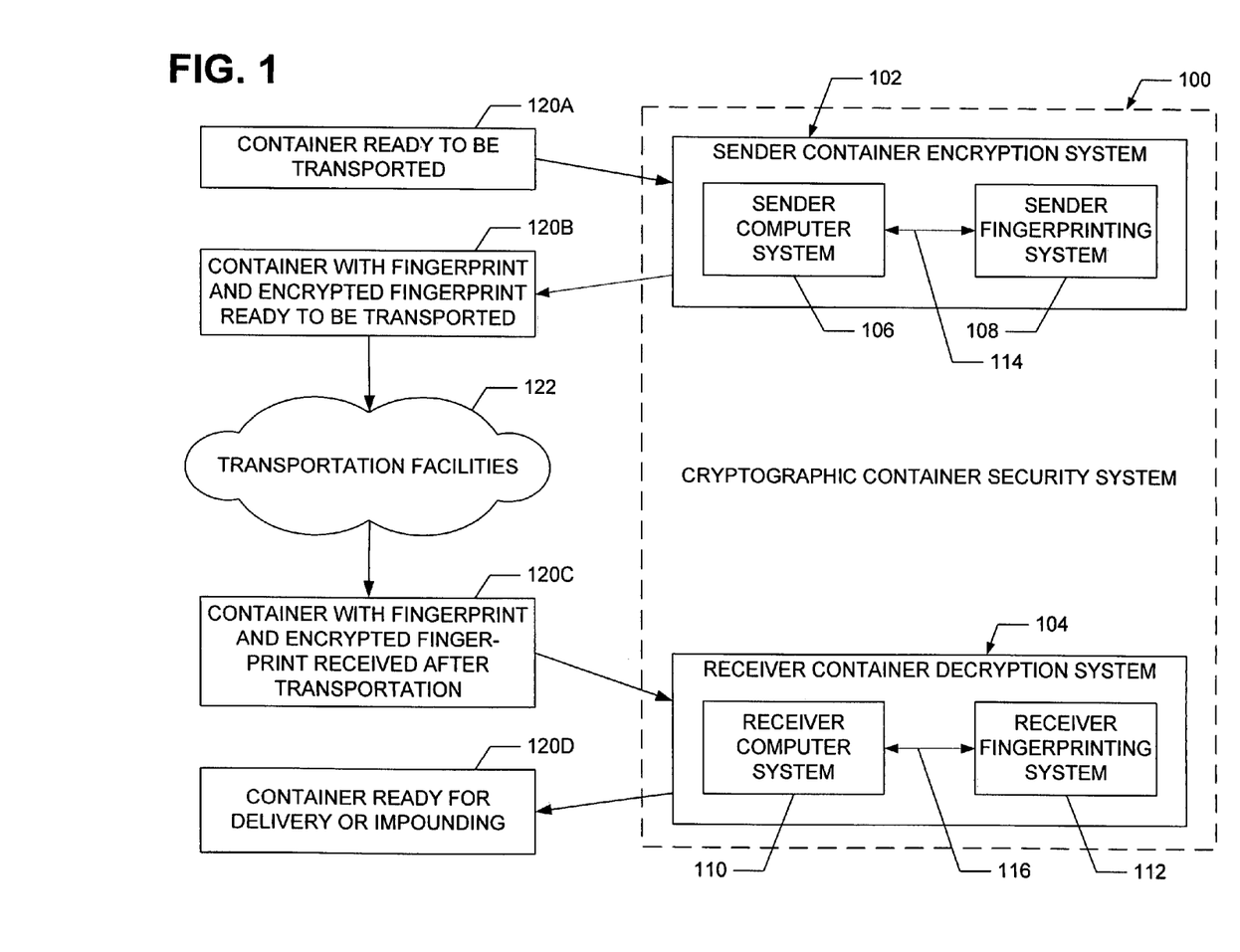
FIG. 1 displays a block diagram representation of the apparatuses of a cryptographic container security system in accordance with an exemplary embodiment of the present invention and an environment therefor.

Referring now to the drawings in which like numerals represent like elements or steps throughout the several views, FIG. 1 displays a cryptographic container security system 100, in accordance with an exemplary embodiment, for aiding in determining whether the contents of a container 120 have been altered during its transportation and in determining whether a received container 120C was digitally signed by the container's original sender as opposed to being digitally signed by an intermediate party. The cryptographic container security system 100 includes a sender container encryption system 102 logically located at a sender site (e.g., the site from which a sender transports a container 120B to a receiver) and a receiver container decryption system 104 logically located at a receiver site (e.g., the site at which a receiver receives the container 120C from a sender after transportation). Generally, the sender and receiver sites comprise seaports, airports, or rail ports, but may, respectively, comprise any other sites from which a container 120 is transported or received after transportation.

The sender container encryption system 102 includes, at least, a sender computer system 106 (also sometimes referred to herein as a "sender computer subsystem") and a sender fingerprinting system 108 that are electrically coupled by one or more communication link(s) 114 for the bi-directional communication of data and control signals therebetween during operation. It should, therefore, be understood that although the sender computer system 106 and sender fingerprinting system 108 are most often located at the same physical site, the sender computer system 106 and sender fingerprinting system 108 may be physically located at different sites by virtue of such communication link(s) 114. The sender computer system 106 generally comprises a computer system having a processing unit for executing computer software, volatile and/or non-volatile memory for temporarily and/or permanently storing computer software and/or data (including, but not limited to, "fingerprint generation software", "encryption software", "fingerprint data", and "fingerprints"), erasable and/or non-erasable media-based storage for temporarily and/or permanently storing computer software and/or data (including, but not limited to, "fingerprint generation software", "encryption software", "fingerprint data", and "fingerprints"), one or more output device(s) such as video displays, printers, or plotters for outputting data or information in a form usable by an operator of the sender container encryption system 102 or other personnel, and one or more communication interfaces for enabling bi-directional communication with the sender container encryption system 102, including, without limitation, communication with the sender fingerprinting system 108 via communication link(s) 114.

The sender computer system 106 is configured to control the operation of the sender fingerprinting system 108 and to receive "fingerprint data", collected, produced, and output by the sender fingerprinting system 108 for and associated with, a container 120A being "fingerprinted" prior to its transportation from the sender site to the receiver site. The sender computer system 106 is also configured to compute a "fingerprint" for a container 120A prior to the container's transportation (sometimes referred to herein as "pre-transportation fingerprint") in accordance with a mathematical fingerprint function or algorithm, F(c), implemented in fingerprint generation software that is stored on and executed by the sender computer system 106, and to output such pre-transportation fingerprint to a media, device, or form that is physically attachable or securable (e.g., as data recorded and present on a computer readable media, as data recorded and present on an electronically, optically, magnetically, electromagnetically, and/or audibly readable media or device, or as data present in another tangible form) to the container 120B and readable by a receiver computer system 110, or another device adapted to read the pre-transportation fingerprint, at a later time. Additionally, in order to improve security even more, the sender computer system 106 may be configured to hash such pre-transportation fingerprint prior to its output by using a hashing algorithm implemented in the fingerprint generation software or other computer software stored on and executed by the sender computer system 106. The sender computer system 106, in addition, is configured to encrypt a computed pre-transportation fingerprint for a container 120A using (i) encryption software stored on and executed by the sender computer system 106 that implements a suitably strong encryption algorithm and (ii) an electronic, or digital, private key ($K_{Priv}$) known only to the sender of the container 120A.

Before proceeding further, it is helpful to define certain terms that are employed and used herein. The term, "fingerprint data", refers to data that identifies, describes, or is representative of objective physical properties or characteristics of a container 120 being transported with such physical properties or characteristics possibly including, without limitation, the container's weight, volume, size-related dimensions, color, construction type, aggregate gamma flux, and aggregate effective Z-number. The term, "fingerprint", refers to the result of a mathematical fingerprint function or algorithm, F(c), that utilizes the fingerprint data for a container 120A,C as operand(s) to compute such result, with the result, as nearly as possible, uniquely identifying the container in a similar manner to the way in which a human fingerprint uniquely identifies a human being. The terms, "fingerprinted" and "fingerprinting", refer to a process of collecting fingerprint data for a container 120A,C before or after it has been transported, as the case may be, and computing a fingerprint using the collected fingerprint data and the mathematical algorithm.

Generally, the fingerprint data to be collected (and/or measured) for a container 120A,C and the mathematical fingerprint function or algorithm, F(c), that utilizes the fingerprint data as operand(s) to generate a fingerprint therefrom, are selected to produce a fingerprint that is as unique as possible for each container 120A,C that is fingerprinted. In choosing the fingerprint data and mathematical fingerprint function, the statistical variance of the mathematical fingerprint function, F(c), for random containers 120A,C should be as large as possible. More specifically, the ideal mathematical fingerprint function, F(c), is bijective, or rather, that $\forall c, c'$; $F(c)=F(c') \leftrightarrow c=c'$; such that F(c) produces a "perfect" fingerprint (where "c" corresponds to the fingerprint data for a container 120B prior to transportation, and "c'" corresponds to the fingerprint data for the same container 120C after transportation). Typically, a highly over-constrained system of fingerprint data provides a suitable fingerprint. In fingerprinting systems similar to those described herein that utilize x-ray scanning of a container 120A,C to collect and/or generate fingerprint data, a suitably secure cryptographic container security system 100 might use a container's aggregate gamma flux, aggregate effective Z-number, mass, and volume as the fingerprint data from which a fingerprint is computed. It should be noted that when x-ray scanning of a container 120A,C is so employed as in the fingerprinting systems described herein, the mathematical fingerprint function, F(c), should not depend upon the internal geometry and/or arrangement of the contents present in a container 120A,C as such contents may shift around or move during the container's transportation.

In selecting an encryption algorithm for implementation in the encryption computer software of the sender computer system 106, the expected distribution over the range of fingerprints must be taken into consideration. If the expected distribution over the range of fingerprints is too small, some encryption algorithms may be vulnerable to "physical dictionary" attacks. Also, the selection of key and fingerprint sizes used in connection with the encryption algorithm should take into account factors such as, but not limited to, the number of containers 120 shipped to a receiver per unit of time, the variance of the mathematical fingerprint function (F(c)), and the expected value of the mathematical fingerprint function (F(c)). If the selected key size is too small or if a bad encryption algorithm is selected, it may be unlikely that a particular container 120 can be tampered with, but may make unaffordably high, the likelihood that some container 120 transported during a reasonably small period of time can be tampered with.

The sender fingerprinting system 108 is configured to measure, collect, and/or generate fingerprint data for and associated with a container 120A prior to its transportation from the sender site to the receiver site and to output such fingerprint data to the sender computer system 106. In accordance with the exemplary embodiment described herein, the sender fingerprinting system 108 comprises an x-ray scanning system (described in more detail below with reference to FIGS. 2 and 3) that generates fingerprint data including an aggregate gamma flux and aggregate effective Z-number for a scanned container. In other embodiments, the sender fingerprinting system 108 may include multiple x-ray scanning systems, scanning systems utilizing other forms of technology, and/or other systems or devices appropriate to measure a container's weight and/or volume, to identify its type and/or color, and/or to measure or collect other objective data for a container 120A that is used by the sender computer system 106 in generating a fingerprint for the container 120A.

As illustrated in FIG. 1, the receiver container decryption system 104 includes, at least, a receiver computer system 110 (also sometimes referred to herein as a "receiver computer subsystem") and a receiver fingerprinting system 112 that are electrically coupled by one or more communication link(s) 116 for the bidirectional communication of data and control signals therebetween during operation. It should, therefore, be understood that although the receiver computer system 110 and receiver fingerprinting system 112 are most often located at the same physical site, the receiver computer system 110 and receiver fingerprinting system 112 may be physically located at different sites by virtue of such communication link(s) 116. Similar to the sender computer system 106 described above, the receiver computer system 110 generally comprises a computer system having a processing unit for executing computer software, volatile and/or non-volatile memory for temporarily and/or permanently storing computer software and/or data (including, but not limited to, fingerprint generation software, decryption software, fingerprint data, and fingerprints), erasable and/or non-erasable media-based storage for temporarily and/or permanently storing computer software and/or data (including, but not limited to, fingerprint generation software, decryption software, fingerprint data, and fingerprints), one or more output device(s) such as video displays, printers, or plotters for outputting data or information in a form usable by an operator of the receiver container decryption system 104 or other personnel, and one or more communication interfaces for enabling bi-directional communication with the receiver container decryption system 104, including, without limitation, communication with the receiver fingerprinting system 112 via communication link(s) 116.

The receiver computer system 110 is configured to control the operation of the receiver fingerprinting system 112 and to receive fingerprint data, collected, produced, and output by the receiver fingerprinting system 112 for and associated with, a container 120C being fingerprinted after its transportation from the sender site to the receiver site. The receiver computer system 110 is also configured to compute a fingerprint for a received container 120C (i.e., a post-transportation fingerprint) using fingerprint data received from the receiver fingerprinting system 112 and fingerprint generation software, and to do so in accordance with the same mathematical fingerprint function or algorithm, F(c), that is employed by the sender container computer system 106 to compute a pre-transportation fingerprint for the same container 120A prior to the container's transportation. Such configuration results from the receiver computer system 110 having stored thereon and executing substantially the same fingerprint generation software as is stored on and executed by the sender computer system 106.

Additionally, the receiver computer system 110 is configured to read, or receive from another communicatively connected device adapted to read, a pre-transportation fingerprint that has been output by a sender computer system 106 to a media, device, or form physically attached or secured (e.g., as data recorded and present on a computer readable media, as data recorded and present on an electronically, optically, magnetically, electromagnetically, and/or audibly readable media or device, or as data present in another tangible form) to a container 120B prior to the container's transportation. The receiver computer system 110 may, in addition, be equipped to read such fingerprint even if it has been hashed using appropriate computer software stored on and executed by the receiver computer system 110. Further, the receiver computer system 110 is adapted to directly or indirectly read and decrypt the encrypted pre-transportation fingerprint from the media, device, or form physically attached or secured to a received container 120C using decryption software stored on and executed by the receiver computer system 110 and an electronic, or digital, public key ($K_{Pub}$) known to the receiver of the container 120C. Still further, the receiver computer system 110 is configured, with appropriate computer software, to compare the post-transportation fingerprint generated for a received container 120C from fingerprint data collected, measured, and/or produced by the receiver fingerprinting system 112 and the pre-transportation fingerprint that was read from the media, device, or form that was physically attached or secured to the received container 120B, to compare the pre-transportation fingerprint read from the media, device, or form that was physically attached or secured to the received container 120B and the decrypted pre-transportation fingerprint read from the same media, device, or form as an encrypted pre-transportation fingerprint and decrypted by the receiver computer system 110, and to inform operators of the receiver container decryption system 104 or other personnel of the results of such comparisons. The operators or other personnel may then take appropriate action with respect to the received container 120C based on the results of such comparison.

In addition to displaying the primary components of the cryptographic container security system 100 of the present invention, FIG. 1 also illustrates the environment in which the cryptographic container security system 100 operates and the movement of an exemplary container 120 relative thereto in connection with a method of the present invention. Therefore, the letter designations (i.e., "A", "B", "C", and "D") following the general element number for a container 120 identify the position of the same container 120 relative to the cryptographic container security system 100 during its processing thereby. Initially, a container 120, including or not including items therein, is ready to be transported from a sender site to a receiver site and is, therefore, designated as "container 120A". The container 120A may include therein many different types of items that are to be transported within the container 120A from the sender site to the receiver site such as, for example and not limitation, furniture, vehicle parts, computers, clothing, food, paper, rugs, carpet, medical supplies and a wide variety of other articles. Generally, the container 120A is secured after being loaded with items to reduce the opportunity for tampering (e.g., the addition of an item, removal of an item, or modification of an item) with the contents thereof during the container's transportation. However, the container 120A has not, at such time, been fingerprinted by the cryptographic container security system 100. It should be understood that the scope of the present invention includes containers 120 that not only include containers 120 typically employed in oceanic commerce, but also containers 120 that comprise, for example and not limitation: containers used in air, rail or truck commerce, piggyback trailers, packages, boxes, suitcases, bags, and any other device, article, or apparatus that may be used to transport items therewithin. It should also be understood that although the present invention is described herein with respect to a single container 120, the cryptographic container security system 100 is operable to process a plurality of containers 120 in a rapid manner and to aid in improving the security of such containers 120, and their contents, during transportation from a sender to a receiver.

Subsequent to the container 120A being present at and ready for transportation from a sender site, the container 120A is processed by the sender container encryption system 102 (described in more detail below) to generate a pre-transportation fingerprint and an encrypted pre-transportation fingerprint that are output to a media, device, or form physically attached or secured to the container 120A. After such processing by the sender container encryption system 102 and upon the physical attaching or securing to the container 120A of the media, device, or form bearing the pre-transportation and encrypted pre-transportation fingerprints, the container 120 is referred to herein as "container 120B" and is transported using transportation facilities 122 from the sender site to a receiver site. Transportation facilities 122 comprise the facilities used to transport a container 120B from a sender site to a receiver site and include, without limitation, the devices and related infrastructure for transportation of the container 120B by: ship, boat, barge, or other water craft; airplane, helicopter, blimp, dirigible, balloon, spaceship, or other aircraft; railroad, truck, trailer, automobile, or other ground craft; and, any combination of the foregoing.

After the container 120B has been transported by whatever transportation facilities 122 and/or method(s) and arrives at the receiver site, the container 120B is then referred to herein as "container 120C" and still has physically attached or secured thereto, the media, device, or form bearing the pre-transportation and encrypted pre-transportation fingerprints generated and output by the sender container encryption system 102. Once the container 120C is received at the receiver site, the container 120C is processed by the receiver container decryption system 104 (as described in more detail below) in order to read the pre-transportation and encrypted pre-transportation fingerprints from the media, device, or form that was physically attached or secured to the container 120B at the sender site, to decrypt the encrypted pre-transportation fingerprint, and to generate a post-transportation fingerprint of the container 120C during such processing. The container 120C, having had a post-transportation fingerprint generated, is then ready for either impounding or delivery based upon the results of further processing performed by the receiver container decryption system 104 and, hence, the container 120C is thereafter referred to herein as "container 120D".

Figure 2:
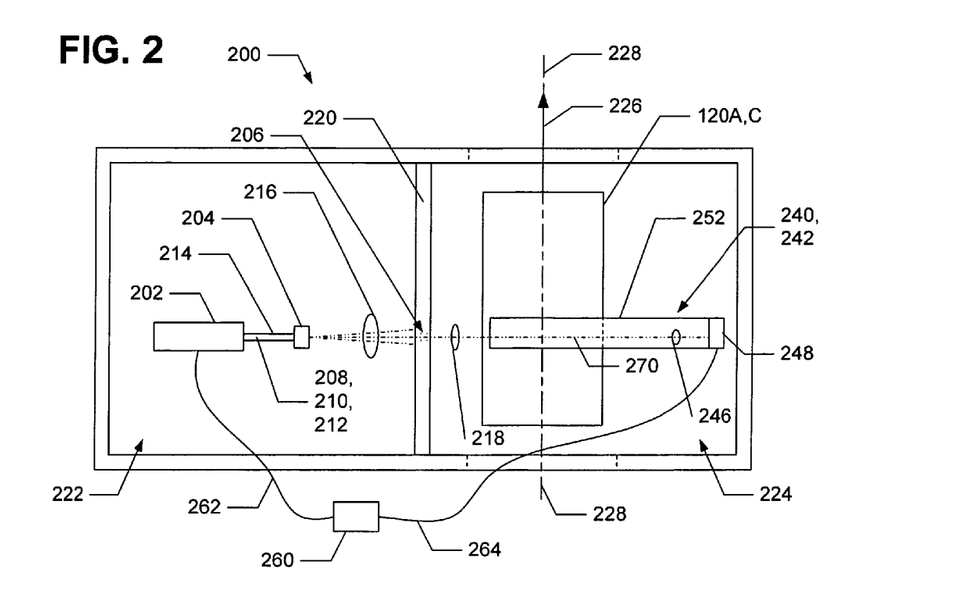
FIG. 2 displays a top, plan, schematic view of the apparatuses of a multi-energy scanning system employed as sender and receiver fingerprinting systems of the cryptographic container security system in accordance with the exemplary embodiment of the present invention.
Figure 3:
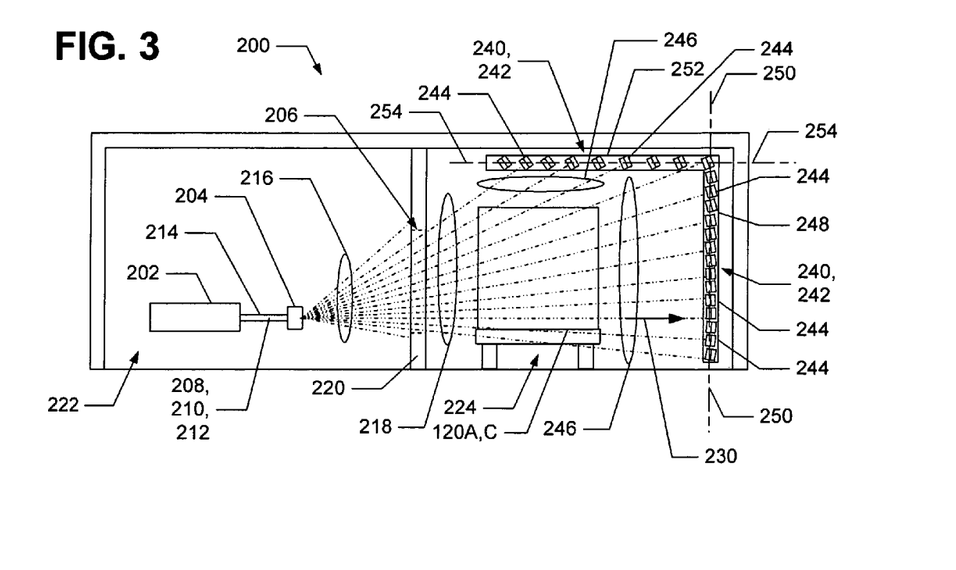
FIG. 3 displays a side, elevational, schematic view of the apparatuses of the multi-energy scanning system of FIG. 2.

FIG. 2 displays a top, plan, schematic view of the apparatuses of a multi-energy scanning system 200 employed as sender and receiver fingerprinting systems 108, 112 of the cryptographic container security system 100 in accordance with the exemplary embodiment of the present invention. Because the sender and receiver fingerprinting systems 108, 112 comprise the same form of system in the exemplary embodiment, only a single description of such system is provided herein. It should be understood, however, that although the present invention is described herein with reference to an exemplary embodiment in which the sender fingerprinting system 108 and the receiver fingerprinting system 112 comprise the same form of system, the scope of the present invention includes sender and receiver fingerprinting systems 108, 112 that may be different in form and technology so long as both systems 108, 112 are capable of generating fingerprint data resulting in the same pre-transportation and post-transportation fingerprints for a container 120 that has not been tampered with during transportation.

The sender and receiver fingerprinting systems 108, 122, according to the exemplary embodiment, each comprise a multi-energy scanning system 200 (also sometimes referred to as a "scanning subsystem") that is operable to expose an entire container 120A,C to bremsstrahlung (e.g., x-rays) having multiple and different spectra, to collect data associated with such exposure(s), and to generate fingerprint data including, without limitation, an aggregate gamma flux and aggregate effective Z-number for the entire container 120A, C, as the case may be. As used herein, the term "aggregate gamma flux" refers to the ratio of the total amount of energy detected by detectors (described below) of the multi-energy scanning system 200 during the time period during which an entire container 120A,C is exposed to the bremsstrahlung (e.g., x-rays) having multiple and different spectra, and the total amount of energy detected by the detectors of the multi-energy scanning system 200 during an equally-long period of time and with the multi-energy scanning system 200 being operated in the same manner, but without a container 120A,C present. In other words, the "aggregate gamma flux" may be thought of as the ratio of the total amount of energy passing through an entire container 120A,C during the time period that the container 120A,C is exposed to the bremsstrahlung having multiple and different spectra, and the total amount of energy present in the generated bremsstrahlung having multiple and different spectra to which the entire container 120A,C was exposed. Further, the term "aggregate effective Z-number" refers to an effective Z-number calculated for an entire container 120A,C such that it is representative of the materials present in the contents within the container 120A,C and in the container 120A,C itself. Notably, neither the aggregate gamma flux nor the aggregate effective Z-number are dependent on the position of the contents within the container 120A,C and, therefore, neither should be effected by the contents of a container 120A,C shifting or moving around within the container 120A,C during transportation thereof.

The multi-energy scanning system 200, as illustrated in FIG. 2, comprises a charged particle accelerator 202, a conversion target 204, and a collimator 206. The charged particle accelerator, in accordance with the exemplary embodiment, includes a pulse-type, multi-energy, linear electron accelerator 202 that is operable to produce, or emit, a pulsed beam of accelerated electrons 208 having a first plurality of pulses of accelerated electrons 210 with a first energy level and a second plurality of pulses of accelerated electrons 212 with a second energy level different from the first energy level. Generally, the energy levels of the pulses 210, 212 are considered to be in the high energy range for a linear accelerator 202, but have appropriate and sufficient spread therebetween such that the bremsstrahlung, or x-ray, spectra resulting therefrom (as described below) may be used for determining effective Z-numbers for materials present in items within a container 120. The individual pulses 210 of accelerated electrons of the first plurality of pulses 210 and the individual pulses 212 of the second plurality of pulses 212 are emitted such that the pulsed beam of accelerated electrons 208 includes successive pulses of accelerated electrons having energy levels that alternate between the first energy level and the second energy level. Thus, each pulse 210 of accelerated electrons of the first plurality of pulses of accelerated electrons 210 having a first energy level is preceded and followed in the pulsed beam of accelerated electrons 208 by a pulse 212 of the second plurality of pulses of accelerated electrons 212 having a second energy level. Similarly, each pulse 212 of accelerated electrons of the second plurality of pulses of accelerated electrons 212 having a second energy level is preceded and followed in the pulsed beam of accelerated electrons 208 by a pulse 210 of the first plurality of pulses of accelerated electrons 210 having a first energy level.

The conversion target 204, as illustrated in FIG. 2, is connected to the output port of accelerator 202 by a vacuum electron beam guide 214 that is adapted to guide, or direct, the pulsed beam of accelerated electrons 208 from the output port of accelerator 202 to the conversion target 204 during operation of the multi-energy scanning system 200. The conversion target 204 is operable to receive pulses of accelerated electrons 210, 212 of the pulsed beam of accelerated electrons 208 and to convert the received pulses of accelerated electrons 210, 212 into a pulsed bremsstrahlung (e.g., x-ray) beam 216 that is output from the conversion target 204 toward the collimator 206. Generally, the pulsed bremsstrahlung beam 216 includes alternating first and second spectra corresponding to the first and second energy levels of the alternating pulses of accelerated electrons 210, 212 of the pulsed beam of accelerated electrons 208 emitted by accelerator 202.

The collimator 206, generally, includes an elongate, narrow opening (e.g., a slot) through which the pulsed bremsstrahlung beam 216 passes to create a shaped bremsstrahlung beam 218 having pulses of bremsstrahlung of alternating spectra with shapes suitable for scanning a container 120A,C. Typically, the shaped bremsstrahlung beam 218 has a fan shape upon exiting the collimator 206. The collimator 206 is, according to the exemplary embodiment, mounted to and/or integrated into a wall 220 separating an accelerator room 222 in which the accelerator 202 and conversion target 204 reside and a scanning room 224 through which a container 120A,C is moved and exposed to the shaped bremsstrahlung beam 218 exiting the collimator 206 during scanning thereof in order to collect data for the generation of aggregate gamma flux and aggregate effective Z-number fingerprint data. During scanning, the container 120A,C is, generally, moved in a substantially linear direction of travel (e.g., indicated by arrow 226) along a longitudinal axis 228 of the scanning room 224 that is substantially collinear with the longitudinal axis of the container 120A,C and substantially perpendicular to the predominant direction of travel of the shaped bremsstrahlung beam 218 (e.g., indicated by arrow 230).

The multi-energy scanning system 200 additionally comprises a detector subsystem 240 having a detector array 242 with a plurality of detectors 244 that are each operable to receive a portion 246 of the shaped bremsstrahlung beam 218 after it passes through a container 120A,C being scanned within the scanning room 224 and to produce electrical signals representative of such portion 246. As displayed in the side, elevational, schematic view of FIG. 3, the plurality of detectors 244 of the detector array 242 are arranged in a, generally, "L" shape with a first portion 248 of the detector array 242 including detectors 244 oriented in a plane 250 substantially perpendicular to the predominant direction of travel of the shaped bremsstrahlung beam 218 (e.g., indicated by arrow 230) and substantially adjacent a side of a container 120A,C as the container 120A,C travels through the scanning room 224. A second portion 252 of the detector array 242 includes detectors 244 oriented in a plane 254 substantially perpendicular to the plane 250 of the first portion 248 of the plurality of detectors 244 such that the second portion 252 extends at least partially above a container 120A,C as the container 120A,C travels through the scanning room 224. In order to enable the reception of the portion 246 of the shaped bremsstrahlung beam 218 that may pass through the top, or roof, of a container 120A,C, some of the individual detectors 244 of the second portion 252 of the detector array 242 are oriented in a direction substantially toward, or facing, the collimator 206 as opposed to being oriented in a direction perpendicular to the top, or roof, of a container 120A,C passing through the scanning room 224.

The multi-energy scanning system 200 further comprises a controller 260 that is connected to the accelerator 202 and to the detector subsystem 240 via bi-directional communication links 262, 264, respectively. The controller 260 is configured with appropriate hardware and software to control the operation of the accelerator 202 in order to appropriately expose a container 120A,C being scanned to the shaped bremsstrahlung beam 218 having multiple and different spectra. Such control is accomplished through operation of the hardware and execution of the software to generate appropriate control signals that are communicated to the accelerator 202 through bi-directional communication link 262. The controller 260 is also configured with appropriate hardware and software to control the operation of the detector subsystem 240 in order to collect data, communicated from the detector subsystem 240 to the controller 260 over bi-directional communication link 264, resulting from the exposure of a container 120A,C to the shaped bremsstrahlung beam 218. The collected data is representative of the portion 246 of the shaped bremsstrahlung beam 218 that exits the container 120A,C and impinges on the detectors 244 of the detector subsystem 240. Additionally, the software of the controller 260 is adapted to generate, upon execution by the controller's hardware, aggregate gamma flux and aggregate effective Z-number fingerprint data for the container 120A,C using the data collected from the detector subsystem 240 and to communicate such fingerprint data to a sender computer system 104 or receiver computer system 110, as the case may be, via an appropriate communication link therebetween.

In operation, the accelerator 202 of the multi-energy scanning system 200 is appropriately controlled by the controller 260, via control signals communicated through bi-directional communication link 262, to produce a pulsed beam of accelerated electrons 208 and direct it at the conversion target 204 through vacuum electron beam guide 214. The pulsed beam of accelerated electrons 208 alternately includes pulses of accelerated electrons 210 having a first energy level and pulses of accelerated electrons 212 having a second energy level. Because the consecutive pulses of accelerated electrons 210, 212 directed at the conversion target 204 alternate between respective different energy levels, the pulsed bremsstrahlung beam 216 produced by and exiting from the conversion target 204 includes pulses of alternating first and second spectra corresponding to the first and second energy levels of the alternating pulses of accelerated electrons 210, 212. The pulsed bremsstrahlung beam 216 is shaped (or, more specifically, the pulses of the pulsed bremsstrahlung beam 216 are shaped) by the collimator 206 to produce the shaped bremsstrahlung beam 218. Similar to pulsed bremsstrahlung beam 216, the shaped bremsstrahlung beam 218 includes pulses of alternating first and second spectra corresponding to the first and second energy levels of the alternating pulses of accelerated electrons 210, 212.

The shaped bremsstrahlung beam 218 having multiple spectra exits the collimator 206 traveling within plane 270 in a direction (e.g., indicated by arrow 230) predominantly perpendicular to the direction of travel of the container 120A,C (e.g., indicated by arrow 226) and impinges upon the container 120A,C as it is moved through the scanning room 224. The shaped bremsstrahlung beam 218 passes through the walls of the container 120A,C and items present in the container 120A,C within plane 270. A portion 246 of the shaped bremsstrahlung beam 218 strikes detectors 244 of the detector array 242 after passing through the walls of the container 120A,C and through items present, if any, in the container 120A,C. The detectors 244 then produce and output data in the form electrical signals representative of and corresponding to the portion 246 of the shaped bremsstrahlung beam 218 impinging thereon and the detector subsystem 240 then communicates such data to the controller 260 via bi-directional communication link 264.

More specifically, on a pulse-by-pulse level, the controller 260 causes the accelerator 202 to generate a pulse of accelerated electrons 210 of a first plurality of pulses of accelerated electrons 210 having a first energy level at a first time. The pulse of accelerated electrons 210 is directed to the conversion target 204 by vacuum electron beam guide 214. Upon receiving the pulse of accelerated electrons 210 having a first energy level, the conversion target 204 converts the received pulse of accelerated electrons 210 into a pulse of bremsstrahlung (e.g., x-rays) having first spectra corresponding to the first energy level of the received pulse of accelerated electrons 210. The conversion target 204 then emits the produced pulse of bremsstrahlung having first spectra in a direction toward the collimator 206. While passing through the collimator 206, the pulse of bremsstrahlung is shaped to produce a shaped pulse of bremsstrahlung having a shape (e.g., a fan shape) suitable for scanning of a container 120A,C being moved through the scanning room 224.

The shaped pulse of bremsstrahlung having first spectra exits the collimator 206 traveling substantially within plane 270 in a direction predominantly perpendicular to the direction of travel of the container 120A,C (e.g., indicated by arrow 226) and impinges upon the container 120A,C as it is moved through the scanning room 224. The shaped pulse of bremsstrahlung passes through the walls of the container 120A,C and through items present, if any, in the container 120A,C substantially within plane 270 (i.e., that is substantially perpendicular to the direction of travel of the container 120A,C). A portion 246 of the shaped pulse of bremsstrahlung passing through the walls of the container 120A,C and items present in the container 120A,C strikes detectors 244 of the detector array 242. The detectors 244 then produce and output, as data, electrical signals representative of and corresponding to the portion 246 of the shaped pulse of bremsstrahlung impinging thereon and, hence, to the materials of the portions of the container 120A,C and of the items within the container 120A,C lying within plane 270 at such first time.

At a second time substantially subsequent to the first time, the controller 260 causes the accelerator 202 to generate a pulse of accelerated electrons 212 of a second plurality of pulses of accelerated electrons 212 having a second energy level different than the first energy level. The pulse of accelerated electrons 212 is guided to the conversion target 204 by vacuum electron beam guide 214.

Similar to the pulse of accelerated electrons 210, upon receiving the pulse of accelerated electrons 212 having a second energy level at the second time, the conversion target 204 converts the received pulse of accelerated electrons 212 into a pulse of bremsstrahlung having second spectra corresponding to the second energy level of the received pulse of accelerated electrons 212. Then, the conversion target 204 emits the produced pulse of bremsstrahlung in a direction toward the collimator 206. While passing through the collimator 206, the produced pulse of bremsstrahlung is shaped to produce a shaped pulse of bremsstrahlung having a beam shape (e.g., a fan shape) suitable for scanning of a container 120A,C continuing to be moved through the scanning room 224.

The shaped pulse of bremsstrahlung having second spectra exits the collimator 206 traveling within plane 270 in a direction predominantly perpendicular to the direction of travel of the container 120A,C (e.g., indicated by arrow 226) and impinges upon the container 120A,C as it is moved through the scanning room 224. The shaped pulse of bremsstrahlung passes through the walls of the container 120A,C and through items present, if any, in the container 120A,C within plane 270. A portion 246 of the shaped pulse of bremsstrahlung passing through the walls of the container 120A,C and items present in the container 120A,C then strikes detectors 244 of the detector array 242. The detectors 244 then produce and output electrical signals representative of and corresponding to the portion 246 of the shaped pulse of bremsstrahlung impinging thereon and, hence, to the materials of the portions of the container 120A,C and of the items within the container 120A,C lying within plane 270 at such second time.

Upon continuous operation of the accelerator 202, conversion target 204, collimator 206, and detector subsystem 240 while the entire container 120A,C travels through the shaped bremsstrahlung beam 218 and plane 270, the controller 260 successively receives sets of output electrical signals from the detectors 244 and detector subsystem 240, via bi-directional communication link 264, that respectively correspond to the successive pulses of the shaped bremsstrahlung beam 218 directed at the container 120A,C and the portions thereof that impinged upon detectors 244 and caused the generation of the electrical signals by the detectors 244 and detector subsystem 240. The controller 260 converts and stores the sets of received electrical signals into data sets in an appropriate form and associates the data sets with respective bremsstrahlung, or x-ray, pulses of the shaped bremsstrahlung beam 218. In other words, the controller 260 associates each data set with the respective pulse that caused its generation and with the energy level and spectra of such pulse. The controller 260 also associates each data set with the location of plane 270 along and relative to the longitudinal axis of the container 120A,C at the time at which such respective pulse was directed at the container 120A,C.

It should be noted that each data set essentially corresponds to a slice being made by plane 270 at a unique location along and perpendicular to the longitudinal axis of the container 120A,C. Therefore, the data of a data set is representative of the materials of the container 120A,C and the contents thereof, if any, at such unique location. Because the container 120A,C moves slightly in the direction of its longitudinal axis between the times at which successive data sets are produced, the data of successive data sets is representative of the materials of the container 120A,C and the contents thereof, if any, at substantially adjacent locations and planes along the longitudinal axis of the container 120A,C. However, because the pulses of the shaped bremsstrahlung beam 218 rapidly alternate between different energy levels relative to the speed of movement of the container 120A,C during scanning thereof, successive data sets associated with pulses of the shaped bremsstrahlung beam 218 having different energy levels may be thought of and analyzed as if the successive data sets correspond to the same location and plane along the longitudinal axis of the container 120A,C.

Using the data of the data sets and the associated data related to the corresponding pulse energy levels and locations along the longitudinal axis of the scanned container 120A,C and by executing appropriate software, the controller 260 produces fingerprint data for the scanned container 120A,C that, in accordance with the exemplary embodiment, includes calculated values of the aggregate gamma flux and aggregate effective Z-number (e.g., which is possible by virtue of the multiple spectra present in the shaped bremsstrahlung beam 218). According to the exemplary embodiment, the aggregate gamma flux is calculated by the controller 260 using the data of the data sets to first determine the total amount of energy present in the portions of the shaped bremsstrahlung beam 218 that passed through the container 120A,C and impinged upon detectors 244 during scanning of the container 120A,C. Then, the controller 260 utilizes the associated data related to the corresponding pulse energy levels to determine the total amount of energy present in the shaped bremsstrahlung beam 218 that was directed at the container 120A,C during scanning thereof. Subsequently, the controller 260 divides the total amount of energy present in the portions of the shaped bremsstrahlung beam 218 that passed through the container 120A,C and impinged upon detectors 244 by the total amount of energy present in the shaped bremsstrahlung beam 218 that was directed at the container 120A,C during scanning. The result of such mathematical division represents the value of the aggregate gamma flux for the scanned container 120A,C.

In accordance with the exemplary embodiment of the present invention, the controller 260 calculates the aggregate effective Z-number for a scanned container 120A,C by executing software that utilizes and implements equations, physics and mathematical analysis, and mathematical relationships associated with multi-energy material recognition as described herein. Generally, the determination of a value for the aggregate effective Z-number of a scanned container 120A,C and its contents, if any, is based upon the physical and mathematical relationships corresponding to the loss of intensity of a bremsstrahlung beam (e.g., an x-ray beam) as it travels through the various materials thereof. For each material traveled through, the bremsstrahlung, or x-ray, beam looses intensity with such loss of intensity being a function of (1) the effective Z-number (e.g., effective atomic number or composition) of the material, (2) the energy of the beam, and (3) the thickness of the material. Thus, if a bremsstrahlung, or x-ray, beam having pulses of multiple energies (or, for that matter, multiple bremsstrahlung, or x-ray, beams each having pulses of a single energy different than that of the pulses of the other beams) is directed through a number of materials and the beam's loss of intensity is measured at each energy, it is possible to solve certain mathematical relationships, or equations, in order to determine the effective Z-numbers and thicknesses of each material encountered by the beam.

If, for the sake of simplicity and descriptive purposes, consideration is given to the determination of the effective Z-number and thickness of a single material through which a bremsstrahlung, or x-ray, beam travels, the final intensity, I (MeV), of the beam emerging from the material may be computed by:

$$I(I_o, \mu, t) = I_o e^{-\mu t}$$

where $I_o$ (MeV) corresponds to the intensity of the beam prior to entering the material, $\mu$ (cm$^2$/g or cm$^{-1}$) corresponds to the material's coefficient of attenuation (described in more detail below), and t corresponds to the material's thickness. Since the material's coefficient of attenuation is dependent upon the material's effective Z-number, Z, and the energy, $E_{ac}$ (Joules), of the bremsstrahlung or x-rays, the final intensity of the beam emerging from the material may be computed by:

$$I(I_o, Z, E_{ac}, t) = I_o e^{-\mu(Z, E_{ac})t}.$$

Based on this relationship, a system of two equations and two unknowns may be obtained from two final intensities, two initial intensities, and the two energies that produced them. The system of two equations may then be solved to determine the material's thickness and effective Z-number.

Before proceeding further, it should be noted that the loss of intensity of a bremsstrahlung, or x-ray, beam traveling through a material results from, among other things, collisions of the beam with the material's atoms. The loss of intensity due to such collisions is mathematically related to the material's coefficient of attenuation, $\mu$. Physically, the material's coefficient of attenuation, $\mu$, is a function of photon cross section, $\sigma$, which is the sum of four properties of the material: (1) photoelectric cross section, $\sigma_\tau$, (2) coherent scattering cross section, $\sigma_{coh}$, (3) incoherent (Compton) scattering, $\sigma_c$, and (4) pair production cross section, $\sigma_\kappa$.

The photon cross section of a particle is an expression of the probability that an incident particle will strike it. As such, photon cross section is strongly related to the total area of a material and the "radius" of the particles within the material. Typically, the photon cross section, $\sigma$, represents the cross-sectional area of a single atom, and consequently, the photon cross section is expressed in units of cm$^2$/atom. Frequently, however, the photon cross section is expressed in units of "barns" instead of cm$^2$, with one barn=$10^{-24}$ cm$^2$.

At the quantum level, the four factors of photon cross section described above, each of which is a function of bremsstrahlung (or x-ray) energy, E, and effective Z-number, comprise terms or operands when computing the photon cross section. Thus, the photon cross section may be expressed as:

$$\sigma(Z, E) = \sigma_\tau(Z, E) + \sigma_{coh}(Z, E) + \sigma_c(Z, E) + \sigma_\kappa(Z, E).$$

It should be noted that although each term of the above equation may be approximated using the relationships described below, large repositories of known photon cross section data exist for many different materials and may be utilized in lieu of such approximations. Interestingly, in the above equation for photon cross section, the photoelectric cross section, $\sigma_\tau$, term dominates at lower bremsstrahlung, or x-ray, energies (e.g., <0.5 MeV). At higher bremsstrahlung, or x-ray, energies (e.g., >5 MeV), the pair production cross section, $\sigma_\kappa$, term dominates. At intermediate bremsstrahlung, or x-ray, energies (e.g., >0.5 MeV and <5 MeV), the coherent scattering cross section, $\sigma_{coh}$, and incoherent (Compton) scattering, $\sigma_c$, terms dominant the equation. Consequently, material recognition and effective Z-number determination techniques vary with the energy level of the utilized bremsstrahlung, or x-ray, beam.

The photoelectric effect upon photon cross section, $\sigma$, results from an x-ray/atom collision in which the incident photon's energy is higher than the binding energy of some electron in the atom of the material. In such a collision, the incident photon of the bremsstrahlung, or x-ray, beam is absorbed and in its place, several fluorescent photons and one electron are ejected, thereby ionizing the atom. Naturally, any bremsstrahlung, or x-ray, that is absorbed does not exit the material and impinge upon a detector.

The photoelectric cross section property of a material, $\sigma_\tau$, may be crudely approximated at low energies (e.g., several KeV to hundreds of KeV) by the following expression:

$$\sigma_\tau(Z, E) \approx 10(Z^5/E^3).$$

The coherent scattering effect upon photon cross section, $\sigma$, results from an incident photon of the bremsstrahlung, or x-ray, beam making a glancing blow off of an atom of a material, thereby deflecting the bremsstrahlung, or x-ray, away from a detector. For bremsstrahlung, or x-ray, wavelengths less than the diameter of the scattering atoms, the coherent scattering cross section property of a material, $\sigma_{coh}$, may be approximated as follows:

$$\sigma_{coh}(Z, E) \approx 8\pi r_e^2 Z^2 (\lambda/(4\pi a Z^{1/3}))^2 (\tfrac{4}{5} - (\lambda/(8aZ^{1/3})))$$

where $\lambda$ is determined by the relationship $E=hc/\lambda$, h is Planck's constant ($6.626068 \times 10^{-34}$ m² kg/s), c is the speed of light ($299{,}792{,}458$ m/s), $r_e$ is the classical electron radius ($2.817940285 \times 10^{-15}$ m), and a=0.885.

The incoherent (Compton) scattering effect upon photon cross section, $\sigma$, results from an incident photon of the bremsstrahlung, or x-ray, beam knocking out a loosely bound electron of an atom of a material and undergoing a direction change (and energy loss) in the process. Since the direction of the incident photon is changed, it will not impinge upon a detector. The incoherent (Compton) scattering property of a material, $\sigma_c$, may be approximated by the following relationship for bremsstrahlung, or x-ray, beams having energy levels in the medium range:

$$\sigma_c(Z, E) \approx 0.665\, Z.$$

Notably, the above approximation of the incoherent (Compton) scattering property, $\sigma_c$, is not substantially effected by the energy of the bremsstrahlung, or x-ray, beam and, thus, the approximation does not include energy as an operand.

The pair production cross section effect upon photon cross section, $\sigma$, at relativistic photon energies (E>$2m_e^2$—where $m_e$ represents the mass of an electron (e.g., $9.10938188 \times 10^{-31}$ kg)) results from an incident photon of the bremsstrahlung, or x-ray, beam impacting an atom of a material and being "consumed" entirely, thereby producing an electron-positron pair.

Thus, for relativistic photon energies, the pair production cross section property of a material, $\sigma_\kappa$, may be approximated proportionally as:

$$\sigma_\kappa(Z, E) \propto Z^2 \ln(E - 2m_e c^2).$$

At very high energies, E, the pair production cross section property of a material, $\sigma_\kappa$, is effectively constant.

As briefly described above, the total (linear) coefficient of attenuation, $\mu_{tot}$, for a particular material is physically a function of photon cross section, $\sigma$, which is calculated as the sum of the (1) photoelectric cross section, $\sigma_\tau$, (2) coherent scattering cross section, $\sigma_{coh}$, (3) incoherent (Compton) scattering, $\sigma_c$, and (4) pair production cross section, $\sigma_\kappa$. Because the photon cross section, $\sigma$, depends on the effective Z-number and the energy, $E_{ac}$, of the bremsstrahlung or x-ray beam, the total (linear) coefficient of attenuation, $\mu_{tot}$, for a particular material is also a function of the effective Z-number and the energy, $E_{ac}$, of the bremsstrahlung or x-ray beam and may be calculated using the following equation:

$$\mu_{tot}(E_{ac}, Z) = \sigma(Z, E_{ac}) \times \rho \times N_A / A$$

where $\mu_{tot}$ is measured in cm$^{-1}$, $\rho$ is the volume density (g/cm³) for an atom of the material, $N_A$ is Avogadro's number ($6.02252 \times 10^{23}$ atom/mole), and A is the atomic mass (g/mole) for the material. Alternatively, the total (linear) coefficient of attenuation, $\mu_{tot}$, may be calculated in cm²/g as follows:

$$\mu_{tot}(E_{ac}, Z) = \sigma(Z, E_{ac}) \times N_A / A.$$

It should be noted that as with photon cross section data, large repositories of pre-computed coefficients of attenuation exist for many materials and energy ranges. Thus, although the total (linear) coefficient of attenuation, $\mu_{tot}$, may be calculated or approximated using the above equations, it may be desirable to use a pre-computed value therefor obtained from such a repository.

With regard to the thickness, t, of a single material through which a bremsstrahlung, or x-ray, beam travels, if the material's length, L, with respect to the direction of travel of the bremsstrahlung, or x-ray, beam is L cm, then t=L. However, if not, the thickness, t, of a single material may be alternatively defined in g/cm² in terms of the material's length, L (cm), and the material's density, $\rho$ (g/cm³), as follows:

$$t = L \times \rho.$$

As also briefly described above, a determination of the effective Z-number and thickness of a single material through which a bremsstrahlung, or x-ray, beam travels may be made using a bremsstrahlung, or x-ray, beam having pulses of multiple energies (or, for that matter, multiple bremsstrahlung, or x-ray, beams each having pulses of a single energy different than that of the pulses of the other beams) that is directed through the material and measuring the beam's loss of intensity at each energy. Viewed slightly differently, if a bremsstrahlung, or x-ray, beam having alternating pulses of multiple energies (e.g., $E_{LO}$ and $E_{HI}$) and correspondingly alternating intensities (e.g., $I_{LOi}$ and $I_{HIi}$) is directed through a single material and at a plurality of detectors, the corresponding final intensities (e.g., $I_{LO}$ and $I_{HI}$) are measurable by the plurality of detectors. Then, the effective Z-number and thickness, t, of the material are determinable using the following system of equations:

$$I_{LO} = I_{LOi} e^{-\mu tot(E_{LO}, Z) t}$$

$$I_{HI} = I_{HIi} e^{-\mu tot(E_{HI}, Z) t}.$$

From these equations, the following equation is obtained:

$$\ln(I_{LO}/I_{LOi})/\ln(I_{Hf}/I_{Hfi}) = \mu_{tot}(E_{LO}, Z)/\mu_{tot}(E_{Hf}, Z).$$

Consequently, the effective Z-number of the material, Z, is obtained by minimizing the following function, F:

$$F(Z) = (\ln(I_{LO}/I_{LOi})/\ln(I_{Hf}/I_{Hfi}) - \mu_{tot}(E_{LO}, Z)/_{tot}(E_{Hf}, Z))^2.$$

Using the effective Z-number of the material, Z, the thickness, t, of the material is then determined by backsolving either of the following equations:

$$t = -\ln(I_{LO}/I_{LOi})/\mu_{tot}(E_{LO}, Z)$$

$$t = -\ln(I_{Hf}/I_{Hfi})/\mu_{tot}(E_{Hf}, Z)$$

It should be noted that the above-described method of determining the effective Z-number and thickness, t, of a material applies only to a single material. If, however, two or more materials were placed in the plane of the bremsstrahlung, or x-ray, beam as is typically encountered with a container 120A,C, the materials would be recognized as a material of a single element and of a single thickness. In order to determine the Z-numbers and thicknesses for each material placed in the plane of the bremsstrahlung, or x-ray, beam, it is necessary to first determine the minimum number of scanning energies required to differentiate m different kinds of material. If m layers of different materials are present in the plane of a bremsstrahlung, or x-ray, beam having pulses at multiple scanning energies and if $Z_i$ and $t_i$ are, respectively, the atomic number and thickness of the ith material, then the final intensities of the pulses striking detectors of a detector subsystem may be computed by:

$$I(I_0, \{Z_i\}, E_{ac}, \{t_i\}) = I_0 \Pi_{1 \leq i \leq m} e^{-\mu(Z, E_{ac})ti}$$

Using this equation, the minimum number of scanning energies required for determining the Z-numbers and thicknesses for each material placed in the plane of the bremsstrahlung, or x-ray, beam may be determined.

Once the minimum number of scanning energies has been determined, principles and equations of absorption edge-based recognition and of scattering resulting from photon-electron collisions may be used to ascertain the Z-numbers and thicknesses of the m different kinds of material placed in the plane of the bremsstrahlung, or x-ray, beam. An absorption edge is a discrete upward spike in the coefficient of attenuation when photon energies are near the binding energies of electrons in the shells of an atom of a material. When the photon energy crosses the binding energy threshold, there is a significantly higher chance that it will ionize the atom. Note that because absorption edges are a photoelectric phenomenon, the energy ranges at which this technique is applicable are in the relatively low photoelectric range.

If the final intensities of the pulses of a bremsstrahlung, or x-ray, beam striking or impinging upon detectors are measured over a range of photon energies, a sharp downward spike will exist at each absorption edge in a material. Because each element above 10 Z has a unique set of absorption edges, measuring final intensities at energies just above and just below these edge energies can yield every element in the path of the beam.

It should be also noted that photon scattering results from a photon-electron collision and that the energy and direction of the scattered photon may be ascertained by modeling the scattering energy and distribution. In order to construct such a model, it is assumed that the impinged upon electron is effectively stationary. If $E_\gamma$ is the energy of an incident photon of a pulse of a bremsstrahlung, or x-ray, beam and if energy and momentum are to be conserved, the following constraints before and after the collision must be obeyed:

$$E_\gamma + m_e c^2 = E'_\gamma + \sqrt{(m_e^2 c^4 + p_e^2 c^2)}$$

$$0 = p'_\gamma \sin \theta_\gamma + p'_e \sin \theta_e$$

$$E_\gamma/c = p'_\gamma \cos \theta_\gamma + p'_e \cos \theta_e$$

where $E'_\gamma$ is the photon energy after collision, $\theta_\gamma$ is the scattering angle for the photon, $\theta_e$ is the scattering angle for the electron, $p'_\gamma$ is the momentum of the photon after the collision, and $p'_e$ is the momentum of the electron after the collision. Notably, for a photon of energy E, $p = E/c$ and $m_e c^2$ is the relativistic rest mass energy of an electron.

From the above, when a photon of energy $E_\gamma$ collides with an atom of a material, the polar angle of scattering for the photon, $\theta$, obeys the following constraint:

$$\cos(\theta) = 1 + (1/E_\gamma - 1/E'_\gamma) m_e c^2$$

where in this case, $E'_\gamma$ is the new energy of the photon. Reformulated, the final energy $E'_\gamma$ as a function of $E_\gamma$ and $\theta$ is:

$$E'_\gamma(E, \theta) = E_\gamma[m_e c^2/(m_e c^2 + E_\gamma(1 - \cos(\theta)))]$$

From this, it is possible to asymptotically bound the energy of a back-scattered photon, even one with "infinite" energy. At its maximal loss of energy, 180 degree ($\pi$ radian) recoil:

$$\lim_{E\gamma \to \infty} E'_\gamma(E_\gamma, \pi) \approx 0.255 \text{ MeV}$$

And, for its maximum back-scatter energy, which happens at a 90 degree ($\pi/2$ radian) deflection:

$$\lim_{E\gamma \to \infty} E'_\gamma(E_\gamma, \pi/2) \approx 0.511 \text{ MeV}$$

Consequently, for worst-case calculations, a maximum photon energy of 0.511 MeV can be used.

When the distribution of the scattering is considered, it becomes useful to speak of the ratio of $(E_\gamma/E'_\gamma)$ after and before collision:

$$P(E_\gamma, \theta) = 1/(1 + E_\gamma/m_e c^2(1 - \cos(\theta)))$$

The above equation for final energy provides the final photon energy for any given angle of scatter. It does not, however, provide the probability that a photon will scatter in any one direction. In order to determine such probability, use of the Klein-Nishina formula of the differential cross section is necessary:

$$d\sigma/d\Omega = 0.5 \, r_e^2 (P(E_\gamma, \theta) - P(E_\gamma, \theta)^2 \sin^2\theta + P(E_\gamma, \theta)^3$$

where, as previously, $r_e$ is the classical electron radius. To understand the meaning of this formula, it is necessary to decompose cross section.

Suppose there is no interest in the probability that a photon scatters at all, but there is interest in the probability that a photon scatters into a particular region. There is some area around the electron that will scatter a colliding photon of a given energy into a particular region. The particular area around the electron is a partial cross section. If the space around an electron is divided into mutually exclusive regions, there is a partial cross section for each region. The sum of such partial cross sections equals the total cross section.

The Klein-Nishina formula provides a way of knowing how the total cross section changes as the size of the region, $\Omega$, measured in steradians, changes. Here, $d\Omega = 2\pi \sin \theta \, d\theta$. Therefore, the Klein-Nishina formula may be interpreted as "the probability that a photon of energy $E_\gamma$ will scatter off an electron and into the region $2\pi \sin\theta\, d\theta$ is $d\sigma/d\Omega$." With this formula, any possible region into which a photon may scatter can be converted to some part of $\Omega$. Then, by integrating, the size of the cross section that will knock photons into that region is determined. Subsequently, the number of photons of a beam of photons that will be knocked into that region may be determined.

Continuing, the ratio of the logarithmic transparencies of a material at two energies, $E_{\gamma 1}$ and $E_{\gamma 2}$, may be expressed as a function of the energies and Z number:

$$\delta(E_{\gamma 1}, E_{\gamma 2}, Z) = \ln(T_1)/\ln(T_2) = \mu_{tot}(E_{\gamma 1}, Z)/\mu_{tot}(E_{\gamma 2}, Z)$$

The transparencies are determined by directing a beam of bremsstrahlung, or x-rays, having pulses of respective energies $E_{\gamma 1}$ and $E_{\gamma 2}$ through a material and toward detectors. If $\delta$, $E_{\gamma 1}$, and $E_{\gamma 2}$ are known, it is possible to solve for the Z-number of the material. Transparency, T, is the inverse of absorption and is a function of photon energy $E_{ac}$, the material's thickness, t, and the material's Z-number as follows:

$$T(E_{ac}, t, Z) = \int_0^{Eac} dP/dE_\gamma(E_{ac}, E_\gamma) e^{-\mu(E\gamma, Z)t} dE_\gamma / \int_0^{Eac} dP/dE_\gamma(E_{ac}, E_\gamma) dE_\gamma$$

Thus, transparency is the ratio of radiation intensity before and after the penetration of a barrier.

In the above equation for transparency, $$dP/dE_\gamma(E_{ac}, E_\gamma) = dI/dE_\gamma(Eac, E_\gamma)(1-e^{-\mu det(E\gamma)tdet})\mu^{en}_{det}(E_\gamma)/\mu_{det}(E_\gamma)$$

Given two experimental transparency measurements, $T_{exp1}$ and $T_{exp2}$, of a material, the material's thickness and Z number may be determined by minimizing (in $\lambda$-calculus notation):

$$\lambda(t,Z)\sqrt{((T(E_{ac1}, t, Z) - T_{exp1})^2 + (T(E_{ac2}, t, Z) - T_{exp2})^2)}$$

Even though there may be multiple solutions to the above expression, a solution may be obtained by trying each discrete Z-number and then searching for the minimal material thickness, t. The transformation to absorption, $\alpha$, from a transparency, T, is:

$$\alpha(T) = (1-\ln(T))$$

Using the above-described analysis, equations, expressions, methods, and software together with the above-described data collected for the scanned container 120A,C, the controller 260 calculates effective Z-numbers at substantially successive locations along the longitudinal axis of the scanned container 120A,C. The controller 260 then calculates an aggregate effective Z-number for the scanned container 120A,C, for example and not limitation, by (i) summing the effective Z-numbers at substantially successive locations or (ii) summing the effective Z-numbers at substantially successive locations and dividing the obtained sum by the number of substantially successive locations. Then, the controller 260 communicates, via appropriate communication link, the values of the aggregate gamma flux and aggregate effective Z-number for the entire scanned container 120A,C as fingerprint data therefor to the server computer system 106 or receiver computer system 110, respectively as the case may be, depending on whether the multi-energy scanning system 200 is employed as a server fingerprinting system 108 or a receiver fingerprinting system 112.

It should be understood that the scope of the present invention encompasses other systems, including apparatuses and methods, for scanning an entire container 120A,C that utilize one or more beam(s) of bremsstrahlung (e.g., x-rays) impinging on the container 120A,C that may each have one or more different spectra. It should also be understood that the scope of the present invention encompasses other systems, including apparatuses and methods, for computing an aggregate gamma flux and/or an aggregate effective Z-number for an entire scanned container 120A,C.

Figure 4A:
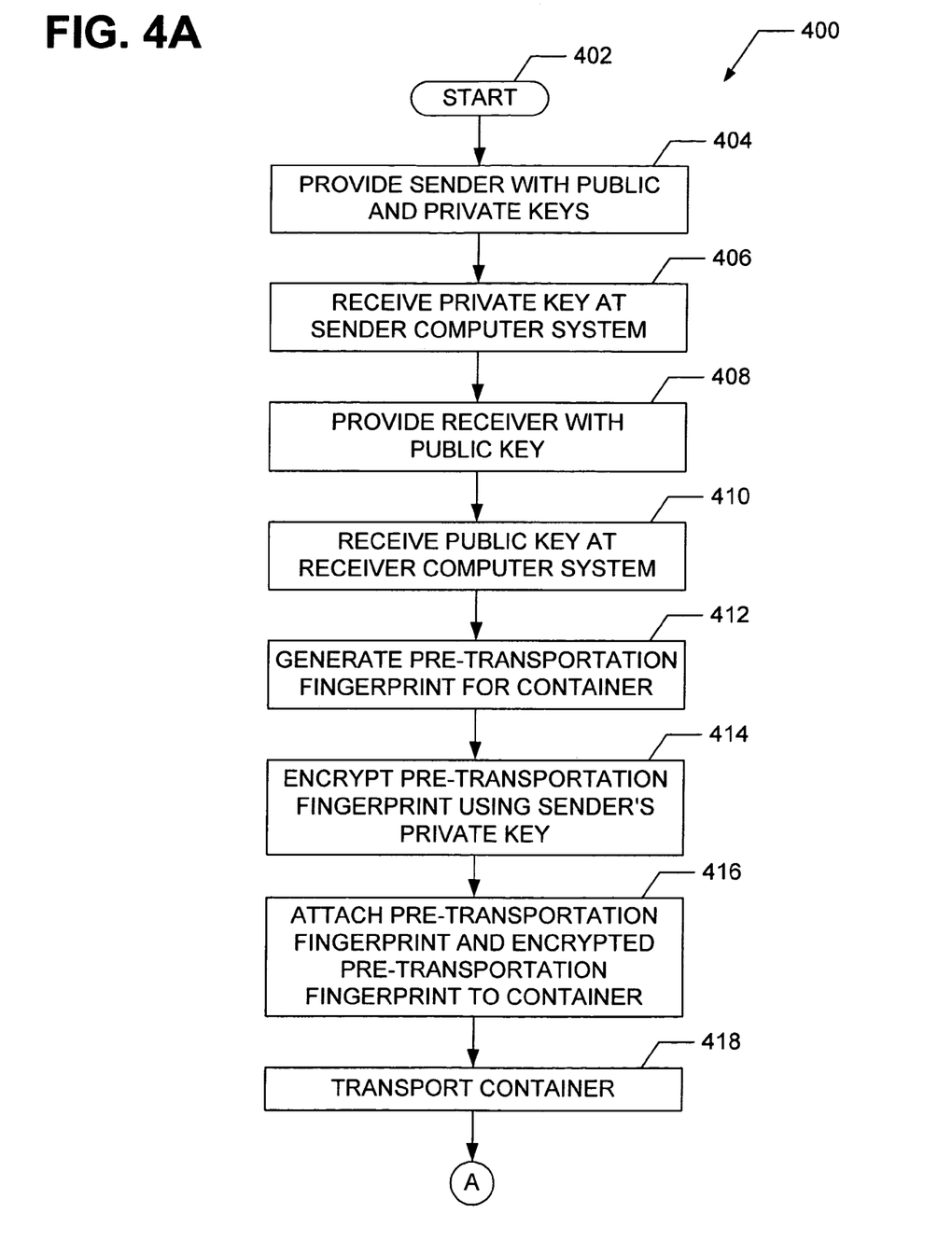
FIGS. 4A and 4B display a flowchart representation of a method of the cryptographic container security system, in accordance with the exemplary embodiment of the present invention, for enabling the secure transportation of a container from a sender site to a receiver site.
Figure 4B:
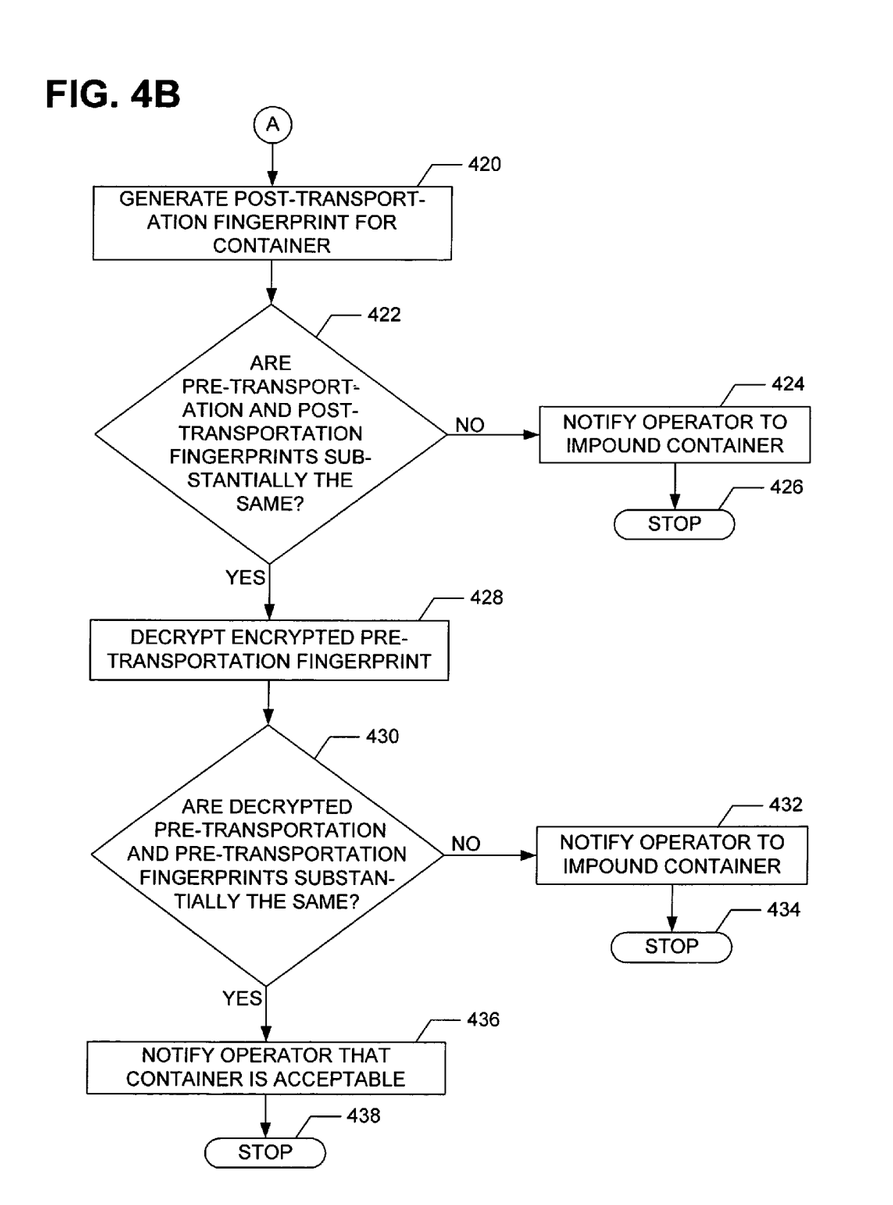

FIGS. 4A and 4B display a flowchart representation of a method 400 of the cryptographic container security system 100, in accordance with the exemplary embodiment of the present invention, for enabling the secure transportation of a container 120B from a sender site to a receiver site. Such secure transportation is enabled, primarily, by determining whether the transported container 120C or its contents have been altered during its transportation and by determining whether the transported container 120C was digitally signed by the container's original sender prior to its transportation. After starting at step 402, the method 400 advances to step 404 where the sender of a container 120A is provided with an electronic, or digital, public key ($K_{Pub}$) and an electronic, or digital, private key ($K_{Priv}$) known only to the sender. The private key ($K_{Priv}$) is subsequently input to the sender computer system 106 by the sender and, at step 406, is received and stored by the sender computer system 106 for future use as described below. Next, at step 408, the receiver is provided with the same digital, public key ($K_{Pub}$) that was provided to the sender at step 404. The public key ($K_{Pub}$) is then input to the receiver computer system 110 by the receiver and, at step 410, is received and stored by the receiver computer system 110 for subsequent use as described in more detail below.

Proceeding to step 412, the sender container encryption system 102 generates a pre-transportation fingerprint for a container 120A to be transported via transportation facilities 122. To generate the fingerprint and in accordance with the exemplary embodiment, the sender fingerprinting system 108 scans the container 120A with a pulsed beam of bremsstrahlung (e.g., x-rays) having pulses of different spectra and generates fingerprint data for the container 120A including, but not limited to, values of the container's aggregate, gamma flux and aggregate effective Z-number. In a different exemplary embodiment of the present invention, the sender fingerprinting system 108 may scan the container 120A with multiple pulsed beams of bremsstrahlung, each having pulses of respectively different spectra, to generate fingerprint data for the container 120A. Regardless of how such fingerprint data is generated, the sender fingerprinting system 108 communicates the fingerprint data for the container 120A to the sender computer system 106 which then, through execution of the fingerprint generation software thereof, generates a pre-transportation fingerprint from the received fingerprint data. If desired for increased security, the sender computer system 106 may subsequently hash the generated fingerprint by executing appropriate computer software that implements a selected hashing algorithm.

After generating (and hashing, if desired) the pre-transportation fingerprint, the sender computer system 106, at step 414, encrypts the generated pre-transportation fingerprint by executing the system's encryption software, retrieving the previously received and stored electronic, or digital, private key ($K_{Priv}$), and using the private key ($K_{Priv}$) as an input to the encryption software. By virtue of such encryption, the sender of the container 120A digitally signs the pre-transportation fingerprint. Next, at step 416, the sender computer system 106 outputs the pre-transportation fingerprint and the encrypted pre-transportation fingerprint to a media, device, or form (e.g., as data recorded and present on a computer readable media, as data recorded and present on an electronically, optically, magnetically, electromagnetically, and/or audibly readable media or device, or as data present in another tangible form) that is physically attachable or securable, directly or indirectly, to the container 120A, and the media, device, or form bearing the pre-transportation fingerprint and encrypted pre-transportation fingerprint are physically attached or secured, directly or indirectly, to the container 120A at the sender site. For example and not limitation, the media, device, or form bearing the pre-transportation fingerprint and encrypted pre-transportation fingerprint may be affixed directly to the container 120A or inserted into a securable receptacle, or holder, such as a lock box that is irremovably affixed to the container 120A and secured, or locked, to limit or restrict access to the media, device, or form and, hence, to the fingerprints.

At step 418, the container 120B with the media, device, or form bearing the pre-transportation fingerprint and encrypted pre-transportation fingerprint physically attached or secured thereto, is transported from the sender site to the receiver site via transportation facilities 122. As described above, such transportation facilities 122 comprise the facilities used to transport the container 120B from the sender site to the receiver site and include, without limitation, the devices and related infrastructure for transportation of the container 120B by: ship, boat, barge, or other water craft; airplane, helicopter, blimp, dirigible, balloon, spaceship, or other aircraft; railroad, truck, trailer, automobile, motorcycle, motor scooter, bicycle, tricycle, moped, or other ground craft; and, any combination of the foregoing.

After being received at the receiver site, the receiver container decryption system 104 generates a post-transportation fingerprint for a container 120C at step 420. To generate the fingerprint and in accordance with the exemplary embodiment, the receiver fingerprinting system 112 scans the container 120C with a pulsed beam of bremsstrahlung (e.g., x-rays) having pulses of different spectra and generates fingerprint data for the container 120C including, but not limited to, values of the container's aggregate gamma flux and aggregate effective Z-number. In a different exemplary embodiment of the present invention, the receiver fingerprinting system 112 may scan the container 120C with multiple pulsed beams of bremsstrahlung, each having pulses of respectively different spectra, to generate fingerprint data for the container 120C. Regardless of how such fingerprint data is generated, the receiver fingerprinting system 112 communicates the fingerprint data for the container 120C to the receiver computer system 110 which then, through execution of the fingerprint generation software thereof, generates a post-transportation fingerprint from the received fingerprint data.

Once the post-transportation fingerprint has been generated, the receiver computer system 110 compares the pre-transportation fingerprint and post-transportation fingerprint at step 422. Such comparison is accomplished by the receiver computer system 110, reading the pre-transportation fingerprint (e.g., with or without the aid of other communicatively connected devices, as necessary) from the media, device, or form physically attached or secured to the container 120C and then mathematically determining whether the pre-transportation and post-transportation fingerprints are substantially the same (i.e., within a reasonable error margin, limit, or constraint). If the pre-transportation and post-transportation fingerprints are not substantially the same, then there is an increased likelihood or probability that the container 120C and its contents have been tampered with during transportation between the sender site and the receiver site, and the receiver computer system 110 branches to step 424 of method 400 where it notifies an operator of the receiver container decryption system 104 and/or other appropriate personnel that the pre-transportation and post-transportation fingerprints are not substantially the same (and that the container 120C has likely been tampered with during transportation) and that the container 120C is to be impounded, as container 120D, for further inspection or processing. The method 400 subsequently stops with respect to such container 120D at step 426.

If, at step 422, it is determined that the pre-transportation and post-transportation fingerprints are substantially the same (i.e., within a reasonable error margin, limit, or constraint), then there is a reduced likelihood or probability that the container 120C has been tampered with during transportation between the sender site and the receiver site and the method 400 continues at step 428 where the receiver computer system 108 decrypts the encrypted pre-transportation fingerprint present in the media, device, or form that was physically attached or secured to the container 120C at the sender site. The receiver computer system 110 does so by reading the encrypted pre-transportation fingerprint (e.g., with or without the aid of other communicatively connected devices, as necessary) from the media, device, or form physically attached or secured to the container 120C, by retrieving from storage the previously received and stored electronic, or digital, public key ($K_{Pub}$), and by then executing decryption software using the retrieved public key as an input thereto.

Continuing at step 430, the receiver computer system 108 mathematically compares the pre-transportation fingerprint and the decrypted pre-transportation fingerprint to determine whether the pre-transportation and decrypted pre-transportation fingerprints are substantially the same (i.e., within a reasonable error margin, limit, or constraint). If not, then the pre-transportation fingerprint of container 120C was not digitally encrypted, or signed, by the true and original sender of the container 120C and the receiver computer system 110 branches to step 432 of method 400 where it notifies an operator of the receiver container decryption system 104 and/or other appropriate personnel that the pre-transportation and decrypted pre-transportation fingerprints are not substantially the same (and that pre-transportation fingerprint of container 120C was not digitally encrypted, or signed, by the true and original sender of the container 120C), that there is an increased likelihood or probability that the container 120C has been tampered with during transportation, and that the container 120C is to be impounded, as container 120D, for further inspection or processing. The method 400 subsequently stops with respect to such container 120D at step 434.

If it is determined by the receiver computer system 110, at step 430, that the pre-transportation and decrypted pre-transportation fingerprints are substantially the same (i.e., within a reasonable error margin, limit, or constraint), then the pre-transportation fingerprint of container 120C was digitally encrypted, or signed, by the true and original sender of the container 120C and the receiver computer system 110, at step 436, notifies an operator of the receiver container decryption system 104 and/or other appropriate personnel of such and that the container 120C is acceptable and ready for opening or delivery as container 120D. The method 400 then stops with respect to such container 120D at step 438.

It should be understood that while method 400 has been described herein with respect to a single container 120 transported from a particular sender site to a particular receiver site, the method 400 may be utilized with respect to a plurality of containers 120 that are transported from a particular sender site to a particular receiver site, to a plurality of containers 120 that are transported from a particular sender site to a plurality of different receiver sites, and to a plurality of containers 120 that are received at a particular receiver site having been transported from a plurality of different sender sites.

Whereas the present invention has been described in detail above with respect to an exemplary embodiment thereof, it should be understood that variations and modifications can be effected within the spirit and scope of the present invention, as described herein before and as defined in the appended claims.

What is claimed is:

1. A method for aiding in the secure transportation of a container used to transport at least one item therein, the method comprising the steps of:
producing pre-transportation data for a container having at least one item present therein at least in part by scanning the container with at least one x-ray beam prior to transportation of the container; and
providing the pre-transportation data to an intended receiver of the container for comparison with post-transportation data for the container produced at least in part by scanning the container with at least one x-ray beam after transportation of the container.

2. The method of claim 1, wherein the pre-transportation data is based at least in part on an aggregate gamma flux for the container and the at least one item present therein.

3. The method of claim 1, wherein the pre-transportation data is based at least in part on an aggregate effective Z-number for the container and the at least one item present therein.

4. The method of claim 1, wherein the pre-transportation data is based at least in part on a mathematical relationship in which at least one of an aggregate gamma flux for the container and an aggregate effective Z-number is an operand.

5. The method of claim 1, wherein the pre-transportation data is reproducible within an acceptable error margin after transportation of the container if the container has not been tampered with during transportation.

6. The method of claim 1, wherein the step of providing the pre-transportation data includes providing the data to an intended receiver of the container in a non-encrypted form.

7. The method of claim 1, wherein the step of providing further includes providing the data to an intended receiver of the container in an encrypted form.

8. The method of claim 1, wherein the at least one x-ray beam includes multiple spectra corresponding to multiple energy levels.

9. The method of claim 1, wherein the step of producing pre-transportation data includes generating the at least one x-ray beam from a charged particle beam having charged particles with multiple energy levels.

10. The method of claim 1, wherein the pre-transportation data is based at least in part on one of the weight of the container, the volume of the container, and a size-related dimension of the container.

11. A method for aiding in the secure transportation of a container used to transport at least one item therein, the method comprising the steps of:
producing post-transportation data for a container having at least one item present therein at least in part by scanning the container with at least one x-ray beam after transportation of the container; and
comparing the post-transportation data for the container with pre-transportation data for the container produced at least in part by scanning the container with at least one x-ray beam prior to transportation of the container.

12. The method of claim 11, wherein the post-transportation data is based at least in part on an aggregate gamma flux for the container and the at least one item present therein.

13. The method of claim 11, wherein the post-transportation data is based at least in part on an aggregate effective Z-number for the container and the at least one item present therein.

14. The method of claim 11, wherein the post-transportation data is based at least in part on a mathematical relationship in which at least one of an aggregate gamma flux for the container and an aggregate effective Z-number for the container is an operand.

15. The method of claim 14, wherein the post-transportation data and the pre-transportation data are based at least in part on the same mathematical relationship.

16. The method of claim 11, wherein the post-transportation data corresponds to the pre-transportation data within an acceptable error margin after transportation of the container if the container has not been tampered with during transportation.

17. The method of claim 11, wherein the step of producing post-termination data includes producing post-termination data at least in part by decrypting previously encrypted pre-transportation data.

18. The method of claim 17, wherein the method further comprises comparing unencrypted pre-transportation data with decrypted previously encrypted pre-transportation data after transportation of the container.

19. The method of claim 11, wherein the at least one x-ray beam includes multiple spectra corresponding to multiple energy levels.

20. The method of claim 11, wherein the post-transportation data is based at least in part on one of the weight of the container, the volume of the container, and a size-related dimension of the container.

21. A system for aiding in the secure transportation of a container used to transport at least one item therein, said apparatus comprising:
a scanning subsystem for scanning a container having at least one item therein with at least one x-ray beam, for generating first data representative of a portion of the x-ray beam passing through said container and said at least one item thereof, and for communicating said first data; and
a computer subsystem communicatively connected to said scanning subsystem for receiving said first data communicated from said scanning subsystem and for producing second data based at least in part on said first data, wherein said second data is for subsequent use at least in part to evaluate the probability that said container has not been tampered with during transportation.

22. The system of claim 21, wherein said first data comprises an aggregate gamma flux for said container and said at least one item therein.

23. The system of claim 21, wherein said first data comprises an aggregate effective Z-number for said container and said at least one item therein.

24. The system of claim 21, wherein said computer subsystem is adapted to encrypt said second data to produce encrypted second data.

25. The system of claim 24, wherein said computer subsystem is further adapted to output said second data and said encrypted second data.

26. The system of claim 21, wherein said computer subsystem is adapted to produce said second data based at least in part on a mathematical relationship in which at least one of an aggregate gamma flux for said container and an aggregate effective Z-number for said container is an operand.

27. The system of claim 21, wherein said computer subsystem is adapted to receive third data representative of at least one of an aggregate gamma flux for said container and an aggregate effective Z-number for said container prior to transportation of said container, and to compare said second data and said third data in order to evaluate the probability that said container has not been tampered with during transportation.

28. The system of claim 21, wherein said computer subsystem is adapted to receive third data representative of at least one of an aggregate gamma flux for said container and an aggregate effective Z-number for said container prior to transportation of said container, to produce fourth data by at least decrypting a first portion of said third data, and to compare a second portion of said third data with said fourth data in order to evaluate the probability that said container has not been tampered with during transportation.

29. The system of claim 21, wherein said scanning subsystem comprises a charged particle accelerator for producing a charged particle beam utilized to generate said at least one x-ray beam, said charged particle beam including at least a first plurality of charged particle pulses having a first energy level and a second plurality of charged particle pulses having a second energy level.

30. The system of claim 21, wherein said at least one x-ray beam includes multiple spectra.

31. The system of claim 21, wherein said computer subsystem is adapted for producing said second data based at least in part on one of the weight of said container, the volume of said container, and a size-related dimension of said container.

* * * * *